(12) United States Patent
Zhang et al.

(10) Patent No.: US 8,831,305 B2
(45) Date of Patent: Sep. 9, 2014

(54) PSEUDO DUAL-ENERGY MATERIAL IDENTIFICATION SYSTEM AND METHOD WITH UNDERSAMPLING

(75) Inventors: Li Zhang, Beijing (CN); Zhiqiang Chen, Beijing (CN); Yuanyuan Liu, Beijing (CN); Yuxiang Xing, Beijing (CN); Ziran Zhao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 494 days.

(21) Appl. No.: 13/322,242

(22) PCT Filed: Dec. 30, 2009

(86) PCT No.: PCT/CN2009/076297
§ 371 (c)(1),
(2), (4) Date: Feb. 7, 2012

(87) PCT Pub. No.: WO2010/135901
PCT Pub. Date: Dec. 2, 2010

(65) Prior Publication Data
US 2012/0134531 A1 May 31, 2012

(30) Foreign Application Priority Data
May 27, 2009 (CN) .......................... 2009 1 0085924

(51) Int. Cl.
*G06K 9/00* (2006.01)
*G01N 23/087* (2006.01)
*A61B 6/03* (2006.01)
*G06T 11/00* (2006.01)
*A61B 6/00* (2006.01)

(52) U.S. Cl.
CPC ........ *G01N 23/087* (2013.01); *G06T 2211/408* (2013.01); *A61B 6/032* (2013.01); *G06T 11/008* (2013.01); *A61B 6/482* (2013.01); *G06T 11/005* (2013.01); *A61B 6/4241* (2013.01); *A61B 6/4035* (2013.01); *A61B 6/4266* (2013.01); *G01N 2223/423* (2013.01)
USPC ........... 382/128; 382/129; 382/131; 382/134; 382/164

(58) Field of Classification Search
USPC .......................................... 382/128–134, 164
See application file for complete search history.

(56) References Cited

U.S. PATENT DOCUMENTS 7,190,757 B2 * 3/2007 Ying et al. ........................ 378/5
7,197,172 B1 * 3/2007 Naidu et al. .................. 382/131

(Continued)

FOREIGN PATENT DOCUMENTS

CN 101237819 8/2008
CN 101433464 5/2009

OTHER PUBLICATIONS

"Improved Single-Pass Split-Merge Image Segmentation in the Application of the Dual Energy CT Reconstruction Method with Reduced Data", by L. Yuan-yuan et al., *China Academic Journal Electronic Publishing House*, Jun. 2009, pp. 86-90.
"A Volumetric Object Detection Framework with Dual-Energy CT", by W. Bi et al., *IEEE*, 2008, pp. 1289-1291.

(Continued)

*Primary Examiner* — Wesley Tucker
(74) *Attorney, Agent, or Firm* — Westman, Champlin & Koehler, P.A.

(57) ABSTRACT

Pseudo dual-energy material identification systems and methods with under-sampling are disclosed. The system comprises a ray generating device, a mechanic rotation control section, a data collecting subsystem comprising a first tier of detectors and a second tier of detectors, and a master control and data processing computer. The system utilizes a CT-imaging-based material identification method with under-sampled dual-energy projection data, in which only a few detectors at the second tier are used to perform dual-energy projection data sampling, and optimization is made on the procedure of solving an equation system.

18 Claims, 8 Drawing Sheets

(56) References Cited

U.S. PATENT DOCUMENTS

| | | | |
|---|---|---|---|
| 8,582,857 B2* | 11/2013 | Chen et al. | 382/131 |
| 2009/0147919 A1* | 6/2009 | Goto et al. | 378/86 |
| 2010/0232669 A1* | 9/2010 | Ziegler et al. | 382/132 |

OTHER PUBLICATIONS

International Search Report from Application No. PCT/CN2009/076297, dated Apr. 8, 2010, 5 pgs.

Written Opinion from Application No. PCT/CN2009/076297, dated Apr. 8, 2010, 5 pgs.

* cited by examiner

PSEUDO DUAL-ENERGY MATERIAL IDENTIFICATION SYSTEM AND METHOD WITH UNDERSAMPLING

CROSS-REFERENCE TO RELATED APPLICATION

This Application is a Section 371 National Stage Application of International Application No. PCT/CN2009/076297, filed 30 Dec. 2009 and published as WO 2010/135901 on Dec. 2, 2010, in Chinese, the contents of which are hereby incorporated by reference in their entirety.

TECHNICAL FIELD

The present invention relates to radiography technology, in particular to improved pseudo dual-energy material identification systems and methods with under-sampling, which enable a rapid and low-cost imaging process in material identification, and thus reduces time and cost in various fields like security inspection.

BACKGROUND

Recently, dual-energy CT imaging technology has been playing an importance role in various fields like security inspection, lossless detection and medical treatment, as it can achieve optimal detection accuracy and enable efficient object reconstruction and material identification.

There are currently two primary implementations for a dual-energy CT imaging method. One of the implementations is a pseudo dual-energy system which performs dual-energy imaging with specifically designed double-tiered detectors, as shown in FIG. 1. In the system of FIG. 1, when scanning is performed, rays penetrate through an object and first arrive at the first tier of low-energy detectors. Then, the rays transmit filtering sheets and finally arrive at the second tier of high-energy detectors. At the same time, respective pixels of two resultant transmission images are automatically in correspondence with identical ray paths.

The other implementation is a real dual-energy system which performs circular scanning on an object using ray sources of different energy levels, as shown in FIGS. 2A and 2B. During the first round of scanning shown in FIG. 2A, the object is scanned with rays at a first energy level. Then, the rays are switched from the first energy level to the second energy level. During the second round of scanning shown in FIG. 2B, the object is scanned with rays at the second energy level. The method shown in FIGS. 2A and 2B requires radiation dose and scanning time two times more than a single-scanning method. Image matching is also required between transmission images of low and high energy levels to ensure pixels of the two images at the same coordinate correspond to the same ray path.

In practical applications, the pseudo dual-energy system is more popular than the real dual-energy system, as it can save up to about half of the scanning time period. Unfortunately, the pseudo dual-energy system requires two tiers of detectors for synchronized data collection and thus costs more than the real dual-energy system. This adversely affects the popularization of the pseudo dual-energy system.

SUMMARY

It is an object of the present invention to provide a pseudo dual-energy material identification system and method with under-sampling, which can achieve a rapid and low-cost material identification by using dual-energy material identification and imaging techniques. Compared with the conventional pseudo dual-energy CT imaging schemes with a full sampling operation, the system according to embodiments of the present invention can substitute the whole second tier of detectors with only a few detectors, and thus effectively reduce the system cost and speed up the identification procedure. The system according to embodiments of the present invention can be applied to various fields including security inspection, lossless detection and medical treatment.

In one aspect of the present invention, a material identification method with under-sampling in a pseudo dual-energy system is provided comprising:

CT scanning an object under inspection, obtaining first projection data with a first tier of detectors in an array to reconstruct a CT image of the object, and obtaining second projection data with a second tier of detectors provided behind a subset of the detectors of the first tier;

combining the first and second projection data to obtain dual-energy under-sampled data at a subset of respective projection angles;

acquiring a photoelectric coefficient integral value and a Compton coefficient integral value from the dual-energy under-sampled data;

segmenting the CT image of the object into a plurality of regions and computing a length by which the dual-energy rays cross each of the regions;

computing the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

computing at least atomic number of material in each of the regions based on the photoelectric coefficient and the Compton coefficient; and identifying the material of the object based on at least the atomic number.

In another aspect of the present invention, a pseudo dual-energy material identification system with under-sampling is provided comprising:

a ray generating device configured to generate ray beams at a first energy level and ray beams at a second energy level, the ray beams being intended to penetrate through an object under inspection;

a mechanic rotation control section comprising a rotation device and a control system and configured to perform a rotatory scanning on the object;

a data collecting subsystem comprising a first array of detectors and a second array of detectors provided behind a subset of the detectors of the first array, and configured to acquire transmission projection data for the ray beams penetrating through the object;

a master control and data processing computer configured to control the ray generating device, the mechanic rotation control section and the data collecting subsystem to CT scan the object, obtain first projection data with a first tier of the detectors of the first array to reconstruct a CT image of the object, and obtain second projection data with a second tier of the detectors of the second array, wherein the master control and data processing computer is configured to:

combine the first and second projection to obtain dual-energy under-sampled data at a subset of respective projection angles;

acquire a photoelectric coefficient integral value and a Compton coefficient integral value from the dual-energy under-sampled data;

segment the CT image of the object into a plurality of segmented regions, and compute a length by which the rays cross each of the regions;

compute the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

compute at least atomic number of material in each of the regions based on the photoelectric coefficient and the Compton coefficient; and identify the material of the object based on at least the atomic number.

Compared with the conventional pseudo dual-energy systems, the above pseudo dual-energy material identification system substitutes a whole tier of detectors with only a few detectors to fulfill the dual-energy material identification and imaging. The proposed system also enables optimization in solving an equation system. Therefore, the system and method according to embodiments of the present invention can reduce the system cost and speed up the identification procedure, thereby making it possible to widely apply the dual-energy material identification and imaging system in practical applications.

The CT-imaging-based material identification scheme with under-sampled dual-energy projections according to the present invention addresses several difficulties in the dual-energy material identification and imaging techniques. It can is fast and less cost, and is thus highly potential for commercial uses.

BRIEF DESCRIPTION OF THE DRAWINGS

The above features and advantages of the present invention will be more apparent from the following detailed description in conjunction with accompanying drawings, in which.

DETAILED DESCRIPTION OF THE PREFERRED EMBODIMENTS

Hereafter, preferred embodiments of the present invention will be elaborated with reference to the figures. Throughout the figures, the same reference sign denotes identical or similar component. For clarity and conciseness, detailed description of any known function and structure herein will be omitted, otherwise the subject matter of the present invention may be obscured.

Figure 1:
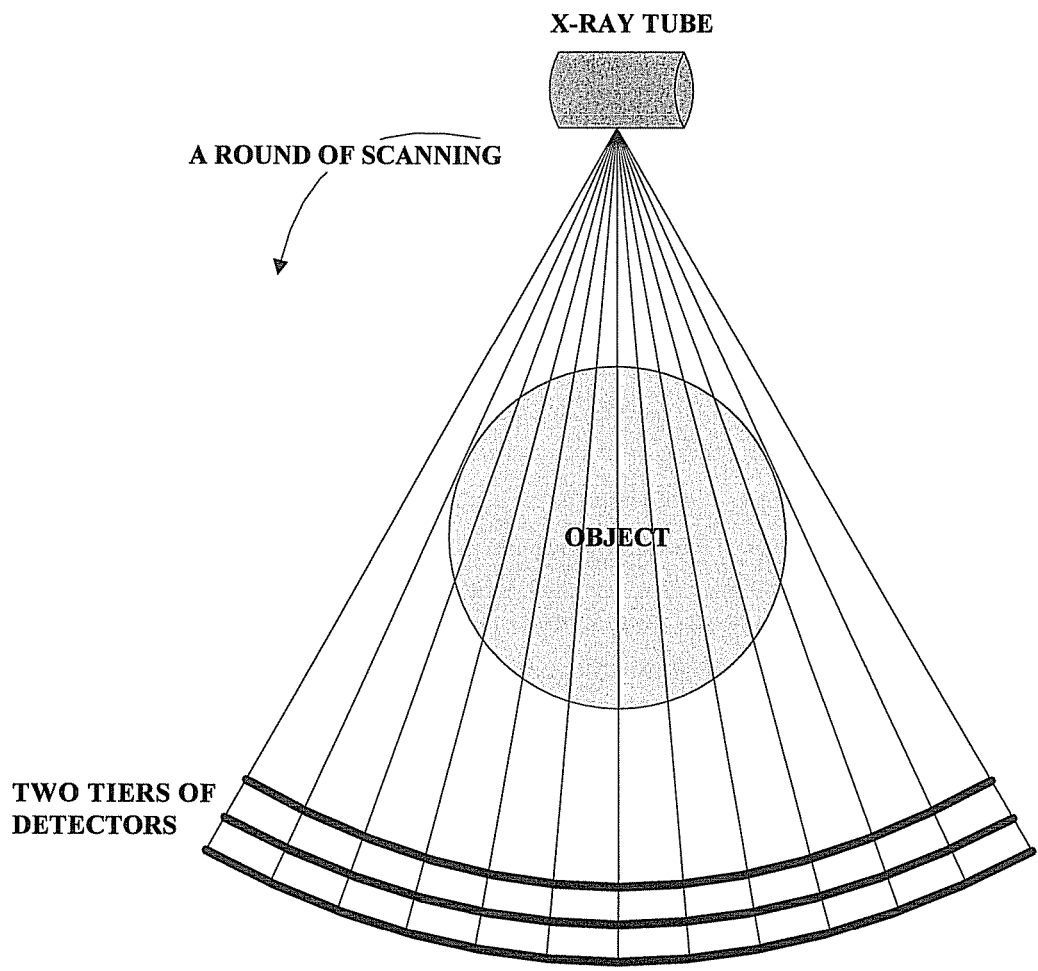
FIG. 1 is a schematic planar diagram showing a circular trajectory scanning of a pseudo dual-energy CT imaging system.
Figure 2A:
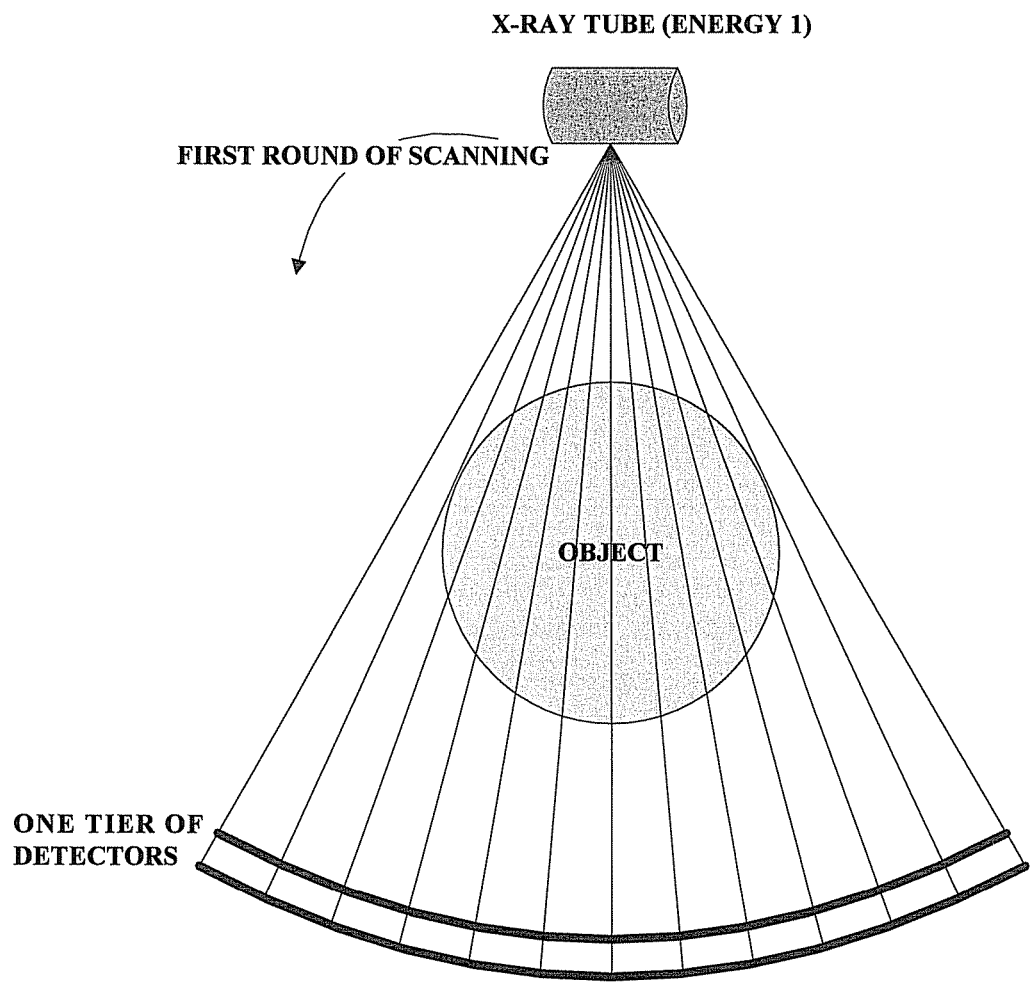
FIGS. 2A and 2B are schematic planar diagrams showing a circular trajectory scanning of a real dual-energy CT imaging system.
Figure 2B:
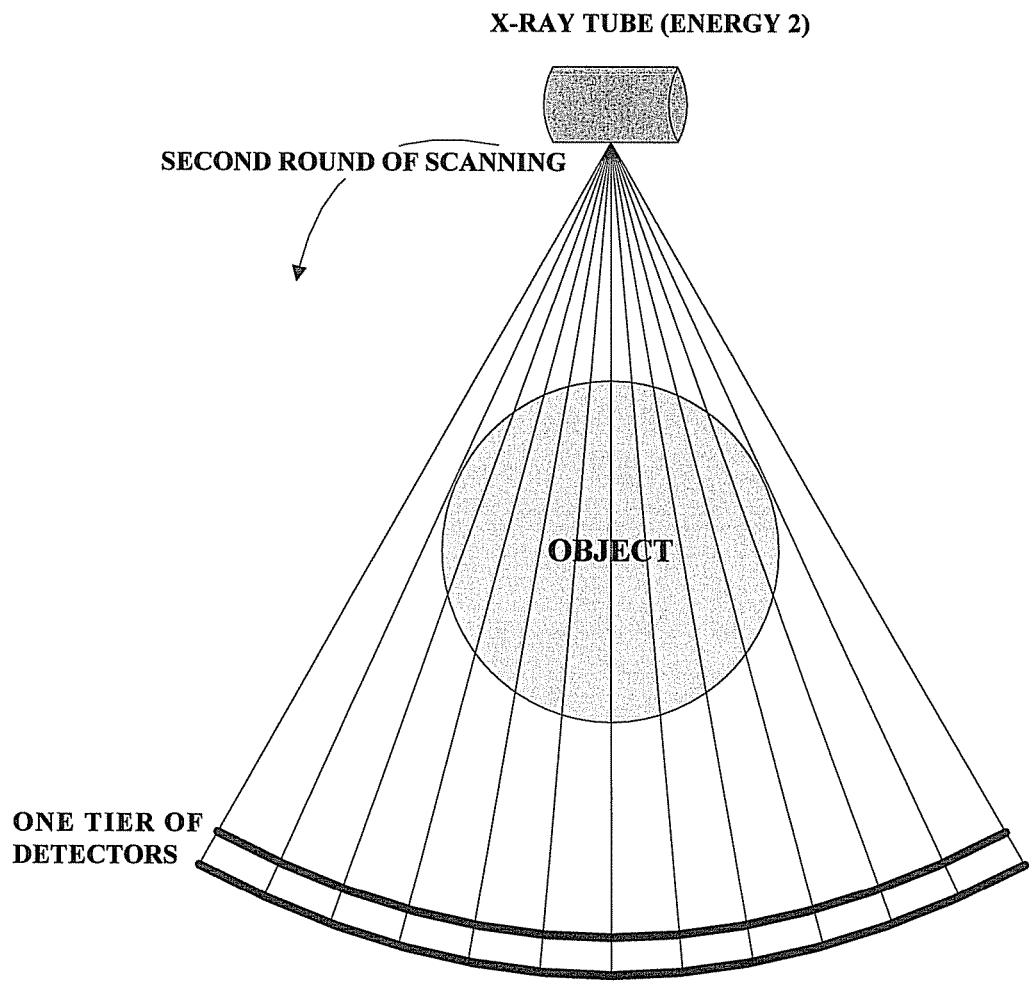
Figure 3A:
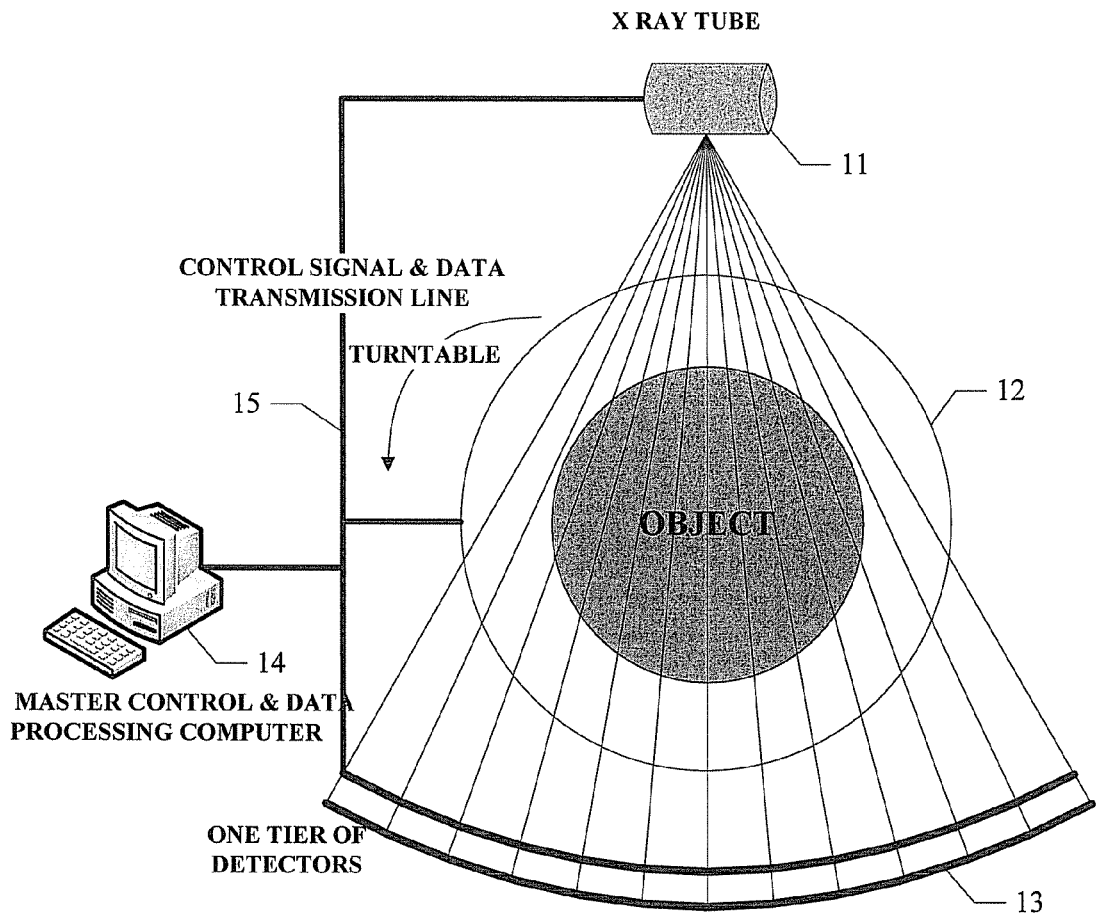
FIGS. 3A and 3B are schematic block diagrams of an improved pseudo dual-energy material system with under-sampling according to an embodiment of the present invention.
Figure 5:
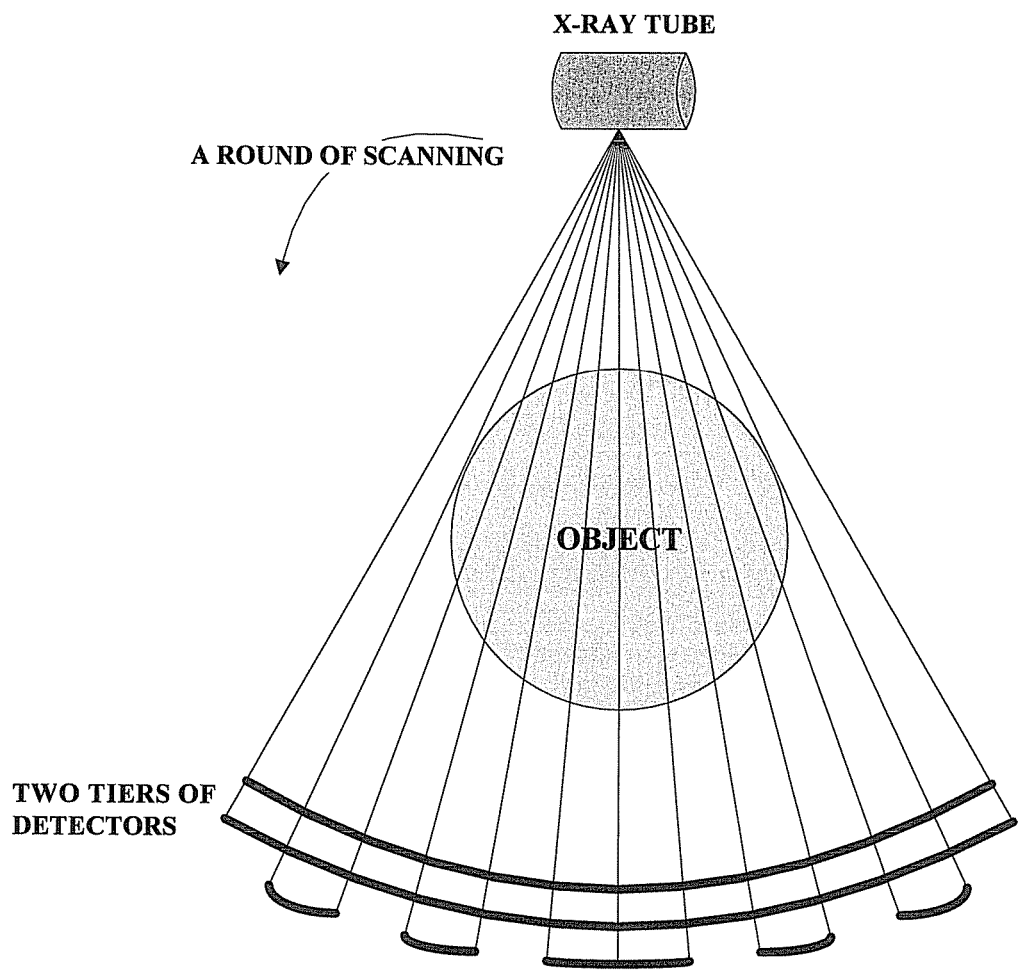
FIG. 5 is a schematic planar diagram showing scanning in a low-cost pseudo dual-energy system for material identification and imaging with under-sampling.

The pseudo dual-energy material identification system with under-sampling according to an embodiment of the present invention implements a CT-imaging-based material identification method with under-sampling of dual-energy projections. As shown in FIGS. 3A and 5, the system reconstructs a CT image of an object under inspection from projection data obtained by scanning with a first tier of detectors, segments the CT image into a number of regions by using an image segmentation method in accordance with attenuation coefficients, and labels these regions. The system also performs dual-energy material imaging and identification by further using projection data obtained by a second tier of a small number of detectors.

The pseudo dual-energy system according to an embodiment of the present invention may be implemented with any one of circular and spiral trajectory scanning. The two implementations are similar and have only two differences which will be described in the following. Hereafter, the pseudo dual-energy system according to an embodiment of the present invention will be introduced taking the circular trajectory scanning as example. As shown in FIG. 3A, the system primarily includes a ray generating device 11, a mechanic rotation control section 12, a data collecting subsystem 13, and a master control and data processing computer 14.

The ray generating device 11 includes an X ray accelerator, an X ray machine, or radioactive isotope, and respective auxiliary equipment. The device 11 can be designed depending on the size of the object under inspection and respective application scenarios.

The mechanic rotation control section 12 includes a rotation device and a control system configured to rotate the object under inspection (or source and detector). The movement of the object is relative to the movement of the source and detector, and thus the two movements are equivalent to each other. In medical treatment, both of source and detectors are usually rotated instead of a patient, because it is not easy for the patient to move. In the present embodiment, the object is rotated.

The data collecting subsystem 13 primarily includes a first tier and a second tier of detectors in an array (generally, the detectors are arranged equidistantly, while they can be arranged equiangularly) for acquiring transmission projection data of the rays. The subsystem 13 further includes sensing circuits, logic control units and the like for projection data on the detectors. The detectors may be solid, gaseous or semiconductor detectors. According to an embodiment, the number of detection cells contained in the second tier of detectors is far less than the number of detection cells contained in the first tier of detectors. In the second tier, the detection cells are provided only behind the end portions and the central portion of the first tier of detectors.

In an embodiment, the second tier of high-energy detection cells are configured such that projection data obtained by each detection cell have a small or minimal correlation with projection data obtained by any other detection cell. For example, the correlation is below a predefined threshold, or the correlation coefficient r for the projection data is minimized.

The array of detectors is stationary, facing the ray source, and located on opposite sides of a turntable. The planar array of detectors is arranged to have as a large angle as possible with respect to the ray source in the horizontal direction, and to have a coverage over the object in the vertical direction.

During the process of data collection, it is required that sampling intervals are uniformly distributed on the time axis, the object moves at a uniform speed, and all of the detectors in the array collect data in a synchronized manner.

The master control and data processing computer 14 sends and receives signals via a control signal and data transmission line 15, and conducts a master control over the operations of the CT system, including mechanic rotation, electrical control, safety interlocking control and the like. The computer 14 processes the projection data acquired by the data collecting subsystem 13. The computer 14 reconstructs a CT image of the object from the projection data collected by the first tier of detectors, segments the image into several regions, and labels these regions. The computer 14 also utilizes the projection data obtained by the second tier of a few detectors for dual-energy material identification and imaging. The computer 14 reconstructs the atomic number and electron density images for materials in the segmented regions for material identification, and displays the images on a display. The computer 14 may be a single Personal Computer (PC) with high performance, or may be a work station or a group of computers.

Figure 3B:
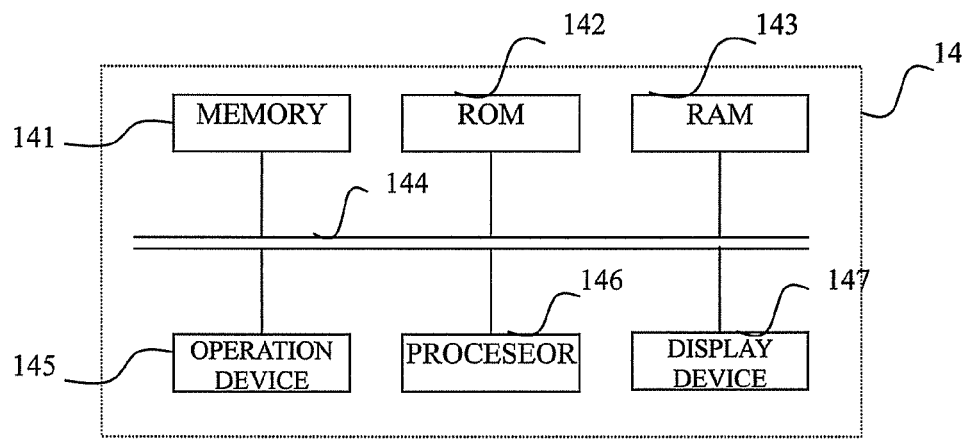

FIG. 3B shows a schematic block diagram of the master control and data processing computer 14 in FIG. 3A. In FIG. 3B, the data collected by the data collecting subsystem 13 are stored in a storage device 141. Read Only Memory (ROM) 142 has stored therein configuration information and program for data processing computer. Random Access Memory (RAM) 143 is configured to temporally store various data during the operation of processor 146. The storage device 141 also stores computer program for data processing and a pre-programmed database. The database maintains information about various known objects, a lookup table for photoelectric coefficient integral values and Compton coefficient integral values, a lookup table or a classification curve for atomic numbers, electron densities for materials, and so on. These items of information are used for comparison with the computed (by the processor 146) attributes (such as atomic number, electron density) of materials in respective regions of the object image. Internal bus 144 connects among the storage device 141, ROM 142, RAM 143, input device 145, processor 146 and display device 147.

After an operator inputs an operation command via the input device 145 such as keyboard or mouse, the processor 146 executes computer program for a predetermined data processing algorithm and obtains a result of data processing. Then, the result is displayed on the display device 147, such as LCD display, or directly outputted in a hardcopy form.

Figure 4:
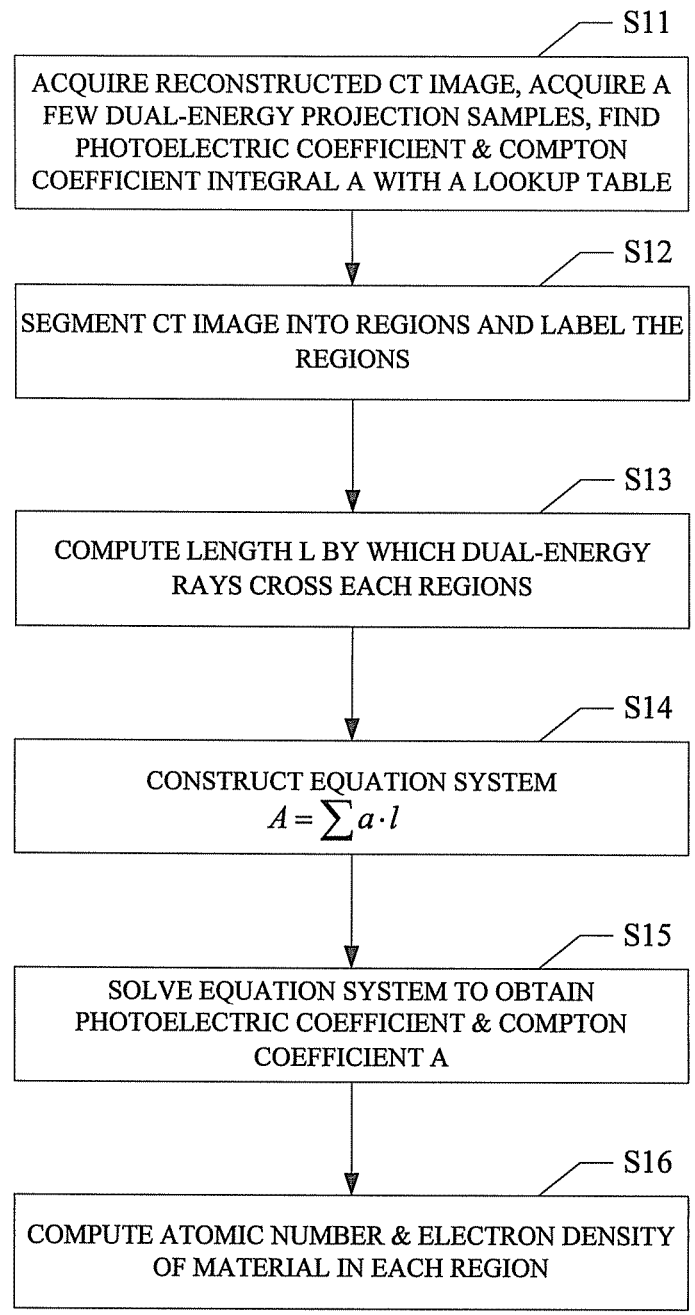
FIG. 4 is a schematic flowchart of a CT-imaging-based material identification method with under-sampled dual-energy projections according to an embodiment of the present invention.

Hereafter, a method according to an embodiment of the present invention will be described with reference to FIG. 4. FIG. 4 shows a schematic flowchart of a material identification method with under-sampled dual-energy projections according to an embodiment of the present invention.

At step S11, the master control and data processing computer 14 controls the ray generating device 11, the mechanic rotation control section 12 and the data collecting subsystem 13 to reconstruct from a CT image of the object from samples of projection data obtained by scanning with the first tier of detectors, in accordance with the circular-trajectory fan-beam reconstruction method (or a spiral-trajectory fan-beam reconstruction method if the trajectory is spiral). Meanwhile, projection data obtained by scanning with the few detectors at the second tier are used as under-sampled dual-energy projection data. Reference may be made to the lookup table to find out photoelectric coefficient integral and Compton coefficient integral A corresponding to each pair of high and low energy projections. It is understood that any other approach can be used to find out the integral A, while the present embodiment is illustrated with the example of using a lookup table.

Figure 6:
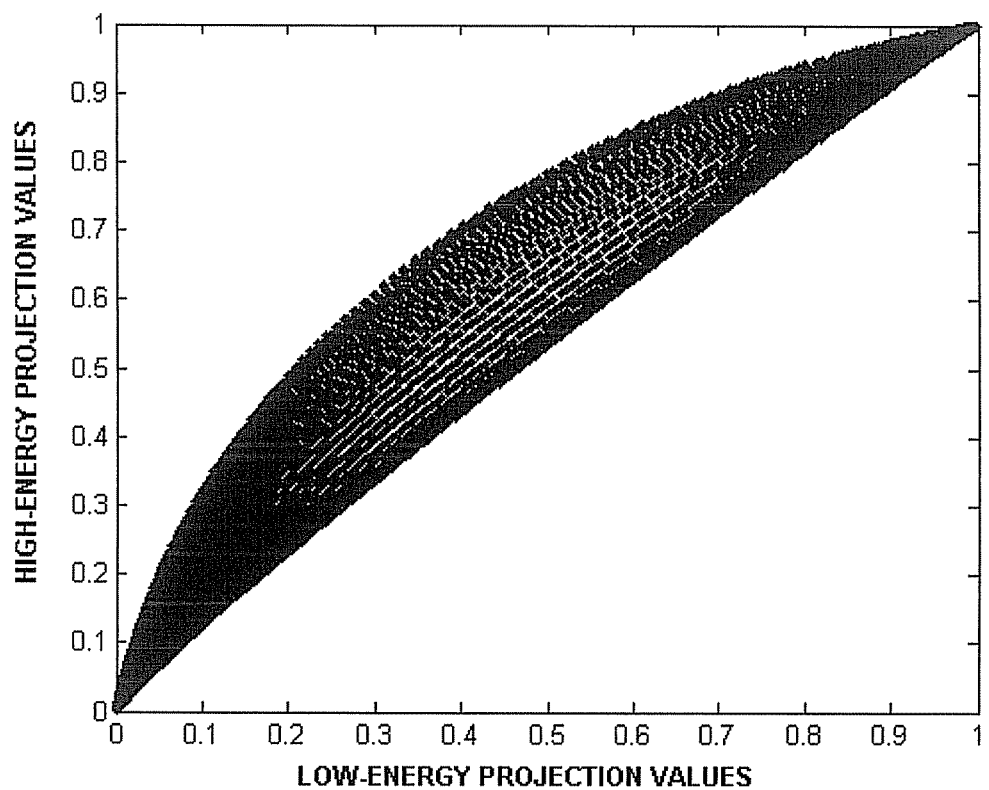
FIG. 6 shows a lookup table of the photoelectric coefficient integral value and the Compton coefficient integral value.

In FIG. 6, the abscissa and ordinate P1, P2 represent projections at low and high energy levels, respectively. At each of the coordinates within the table, there is a value for photoelectric coefficient integral and Compton coefficient integral A corresponding to the high and low energy projection data. When the high and low energy projection data are given, the value for photoelectric coefficient integral and Compton coefficient integral A can be obtained by looking up the table. More details of such lookup table can be found in a document titled "A Volumetric Object Detection Framework with Dual-Energy CT", IEEE NSS/MIC 2008.

At step S12, the master control and data processing computer 14 divides the reconstructed CT images into several individual regions based on the grayscale differences between these regions by using the technique of image segmentation, and labels the divided regions. The technique of image segmentation may be, for example, a modified one-way split-and-merge approach.

Figure 7:
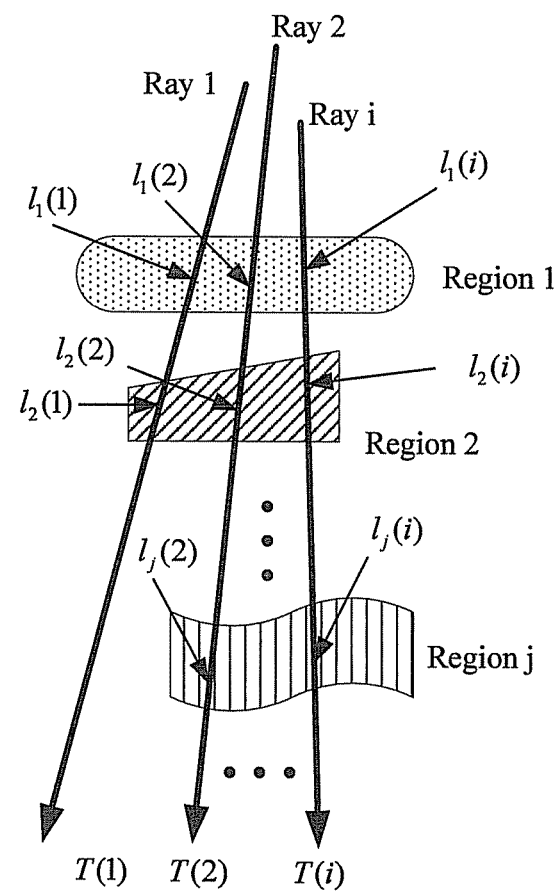
FIG. 7 is a schematic diagram depicting computation of lengths of rays crossing the segmented regions.

In FIG. 7, $l_j(i)$ represents the length by which the ith ray crosses the jth region, and T(i) represents projection data. At step S13, the planar length $l_j(i)$ by which the ray beams corresponding to the ith set of projection data crosses the jth region (or the spatial length $l_j(i)$ by which the ray beams corresponding to the ith set of projection data crosses the jth region, if the trajectory is spiral) is computed on the basis of the samples of dual-energy projections obtained at step to S11.

At step S14, by using the dual-energy preprocessing dual-effect decomposition reconstruction method, the master control and data processing computer 14 establishes a equation system $A=\Sigma a \cdot l$, where a represents Compton coefficient and photoelectric coefficient. It is assumed that M sets of high- and low-energy projection data are obtained after the first round of scanning by the second tier of detectors, the CT image are segmented into N labeled regions, and $T_H(i)$ and $T_L(i)$ represent the ith sets of high- and low-energy projection data. Then, the dual-effect decomposition is performed on linear attenuation coefficients according to the following formula (1):

$$\mu(E)=a_1 f_{ph}(E)+a_2 f_{KN}(E) \qquad (1)$$

Further, the high- and low-energy transparency are represented by the following formulas (2) and (3):

$$T_H = \int_{E_H} D_H(E)\exp\left(-\int \mu(E)dl\right)dE \qquad (2)$$
$$= \int_{E_H} D_H(E)\exp(-A_1 f_{ph}(E) - A_2 f_{KN}(E))dE$$

$$T_L = \int_{E_L} D_L(E)\exp\left(-\int \mu(E)dl\right)dE \qquad (3)$$
$$= \int_{E_L} D_L(E)\exp(-A_1 f_{ph}(E) - A_2 f_{KN}(E))dE$$

wherein $f_{ph}(E)$ represents dependence of the photoelectric section on the ray energy E, $f_{KN}(E)$ describes the relationship between the Compton section and the photon energy, $D_H(E)$ represents the energy spectrum of the X rays detected by the high-energy detectors, $D_L(E)$ represents the energy spectrum of the X rays detected by the low-energy detectors, $a_1$ represents photoelectric coefficient, $a_2$ represents Compton coefficient, $A_1$ represents photoelectric coefficient integral, and $A_2$ represents Compton coefficient integral. The integral is represented by the formula (4):

$$A = \int a \, dl \quad (4)$$

Then a linear equation system is established as:

$$A = \Sigma a \cdot l \quad (5)$$

More specifically, $a_1$ and $a_2$ are computed with the following systems of equations (6) and (7):

$$\begin{bmatrix} l_1(1) & l_2(1) & \cdots & \cdots & l_N(1) \\ l_1(2) & \ddots & & & \vdots \\ \vdots & & \ddots & & \vdots \\ \vdots & & & \ddots & \vdots \\ l_1(M) & \cdots & \cdots & \cdots & l_N(M) \end{bmatrix} \begin{bmatrix} a_{1,1} \\ a_{1,2} \\ \vdots \\ \vdots \\ a_{1,N} \end{bmatrix} = \begin{bmatrix} A_1(1) \\ A_1(2) \\ \vdots \\ \vdots \\ A_1(M) \end{bmatrix} \quad (6)$$

$$\begin{bmatrix} l_1(1) & l_2(1) & \cdots & \cdots & l_N(1) \\ l_1(2) & \ddots & & & \vdots \\ \vdots & & \ddots & & \vdots \\ \vdots & & & \ddots & \vdots \\ l_1(M) & \cdots & \cdots & \cdots & l_N(M) \end{bmatrix} \begin{bmatrix} a_{2,1} \\ a_{2,2} \\ \vdots \\ \vdots \\ a_{2,N} \end{bmatrix} = \begin{bmatrix} A_2(1) \\ A_2(2) \\ \vdots \\ \vdots \\ A_2(M) \end{bmatrix} \quad (7)$$

At step S15, the systems of equations established at step S14 are solved to obtain the solution of a, i.e., photoelectric coefficient $a_1$, and Compton coefficient $a_2$. Then, at step S16, atomic number and electron density are computed with the formulas (8) and (9):

$$a_1 \approx K_1 \frac{N_A}{2} \rho Z^n (n \approx 3) \quad (8)$$

$$a_2 \approx K_2 \frac{N_A}{2} \rho \quad (9)$$

wherein Z represents atomic number, $\rho$ represents electron density, $N_A$ represents Avogadro constant, $K_1$ is a constant including all other coefficients independent from ray energy and material parameter, $K_2$ is also a constant including all other coefficients independent from ray energy and material parameter. Accordingly, the atomic number and the electron density of material in each of the divided region can be computed, and the material can be effectively identified. For example, a lookup table or a classification curve can be used to identify the material in each of the regions with the computed atomic number. Alternatively, both of the computed atomic number and electron density may be used to identify the material.

At step S15 of solving the equation system, the least square method is directly applied. However, it is known that in a normal 360-degree circular scanning, a total of 360 samples will be obtained if scanning is performed once for each 1-degree rotation. At the same time, 360 pieces of projection data multiplied by the number of the detectors at the second tier will be obtained for each sampling process. Accordingly, the number M of the dual-energy projection data will be above the order of 100K. Such huge amount of computation will severely prolong the time required for computation. In addition, because these projection data are densely collected, the correlation among the equations is very high.

The method and system according to embodiments of the present invention can also optimize step S15 of solving the equation system, in addition to the use of CT-imaging-based material identification with under-sampled dual-energy projection data. In this way, the system of the embodiments can address the issue in a faster way. The optimization can be performed as follows.

First stage: after one round of 360-degree scanning, dual-energy projection data are obtained by combining the projection data obtained by the few detectors at the second tier and the project data obtained by the corresponding ones from the first tier of detectors. Then, rays are classified into different categories, and the rays in one category have the same property in terms of the lengths $l_j(i)$ by which the ray beams corresponding to the obtained dual-energy projection data cross the respective regions (the property refers to how many regions a ray beam travels across, for example, one region, two regions, ..., N regions). A single straight ray is taken from each category to represent information of all the rays having the same property as the taken ray, and a new matrix is established having M' elements. The corresponding photoelectric coefficient integral value and Compton coefficient integral value are $A'_1$ and $A'_2$, respectively.

Second stage: the equation system with the newly established matrix of M' elements is solved using the least square method to obtain approximations of $a_1$ and $a_2$. The solving procedure is completed.

The material identification, imaging and detection system according to the embodiments of the present invention uses a CT-imaging-based material identification method with under-sampled dual-energy projection data. In the method, only a few detectors are provided at the second tier for dual-energy data sampling, and the procedure of solving the equation system in the method is also optimized. This provides dual-energy material identification and imaging of low cost and fast speed. The method and system according to the embodiments of the present invention are applicable in various fields like security inspection, lossless detection and medical treatment.

The foregoing description is only made to the embodiments of the present invention. It should be noted to those ordinarily skilled in the art that various modifications and refinements can be made within the principle of the present invention and should be encompassed by the scope of the present invention. The scope of the present invention is defined by the appended claims.

What is claimed is:

1. A material identification method with under-sampling in a pseudo dual-energy system is provided comprising:
   CT scanning an object under inspection, obtaining first projection data with a first tier of detectors in an array to reconstruct a CT image of the object, and obtaining second projection data with a second tier of detectors provided behind a subset of the detectors of the first tier;
   combining the first and second projection data to obtain dual-energy under-sampled data at a subset of respective projection angles;
   acquiring a photoelectric coefficient integral value and a Compton coefficient integral value from the dual-energy under-sampled data;
   segmenting the CT image of the object into a plurality of regions and computing a length by which the dual-energy rays cross each of the regions;
   computing the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

computing at least atomic number of material in each of the regions based on the photoelectric coefficient and the Compton coefficient; and identifying the material of the object based on at least the atomic number.

2. The method of claim 1, wherein the step of computing at least atomic number comprises computing the atomic number and the electron density of the material in each region, and the step of identifying comprises identifying the material of the object based on the atomic number and the electron density.

3. The method of claim 1, wherein the step of identifying comprises determining the material of the object in each of the regions by using a lookup table.

4. The method of claim 1, wherein the step of identifying comprises determining the material of the object in each of the regions by using a pre-established classification curve.

5. The method of claim 1, wherein the projection data obtained by the second tier of detectors comprise projection data at a single projection angle.

6. The method of claim 1, wherein the projection data obtained by the second tier of detectors comprise projection data at several projection angles, and correlation among the projection data at the several projection angles is less than a predefined threshold value.

7. The method of claim 1, further comprising a step of labeling the segmented regions.

8. The method of claim 1, wherein the step of segmenting the CT image and computing the length further comprises:

classifying rays into different categories, with the rays in one category having the same property in terms of the lengths by which the ray beams corresponding to the dual-energy projection data cross the respective regions, wherein the dual-energy projection data are obtained after one round of 360-degree scanning by combining the projection data obtained by the detectors at the second tier and the project data obtained by the corresponding ones from the first tier of detectors; and taking a single straight ray from each category to represent information of all the rays having the same property as the taken ray to establish a new matrix;

the step of computing the photoelectric coefficient and the Compton coefficient further comprises:

solving the equation system with the above established matrix using the least square method to obtain the photoelectric coefficient and the Compton coefficient.

9. The method of claim 1, wherein the detectors at the second tier are provided behind the detectors at the end parts and the central part of the first tier.

10. A pseudo dual-energy material identification system with under-sampling, comprising:

a ray generating device configured to generate ray beams at a first energy level and ray beams at a second energy level, the ray beams being intended to penetrate through an object under inspection;

a mechanic rotation control section comprising a rotation device and a control system and configured to perform a rotatory scanning on the object;

a data collecting subsystem comprising a first tier of detectors and a second tier of detectors provided behind a subset of the detectors of the first tier, and configured to acquire transmission projection data for the ray beams penetrating through the object;

a master control and data processing computer configured to control the ray generating device, the mechanic rotation control section and the data collecting subsystem to CT scan the object, obtain first projection data with a first tier of the detectors to reconstruct a CT image of the object, and obtain second projection data with a second tier of the detectors, wherein the master control and data processing computer is configured to:

combine the first and second projection to obtain dual-energy under-sampled data at a subset of respective projection angles;

acquire a photoelectric coefficient integral value and a Compton coefficient integral value from the dual-energy under-sampled data;

segment the CT image of the object into a plurality of segmented regions, and compute a length by which the rays cross each of the regions;

compute the photoelectric coefficient and the Compton coefficient by way of dual-energy preprocessing dual-effect decomposition reconstruction method, based on the lengths of the rays crossing the regions, the photoelectric coefficient integral value and the Compton coefficient integral value;

compute at least atomic number of material in each of the regions based on the photoelectric coefficient and the Compton coefficient; and identify the material of the object based on at least the atomic number.

11. The system of claim 10, wherein the master control and data processing computer is further configured to compute the atomic number and the electron density of the material in each region, and identify the material comprises a unit configured to identify the material of the object based on the atomic number and the electron density.

12. The system of claim 10, wherein the master control and data processing computer is further configured to determine the material of the object in each of the regions by using a lookup table.

13. The system of claim 10, wherein the master control and data processing computer is further configured to determine the material of the object in each of the regions by using a pre-established classification curve.

14. The system of claim 10, wherein the projection data obtained by the second tier of detectors comprise projection data at a single projection angle.

15. The system of claim 10, wherein the projection data obtained by the second tier of detectors comprise projection data at several projection angles, and correlation among the projection data at the several projection angles is less than a predefined threshold value.

16. The system of claim 10, wherein the master control and data processing computer is further configured to label the segmented regions.

17. The system of claim 10, wherein the master control and data processing computer is further configured to:

classify rays into different categories, with the rays in one category having the same property in terms of the lengths by which the ray beams corresponding to the dual-energy projection data cross the respective regions, wherein the dual-energy projection data are obtained after one round of 360-degree scanning by combining the projection data obtained by the detectors at the second tier and the project data obtained by the corresponding ones from the first tier of detectors; and take a single straight ray from each category to represent information of all the rays having the same property as the taken ray to establish a new matrix;

the master control and data processing computer is further configured to compute the photoelectric coefficient and the Compton coefficient by solving the equation system with the above established matrix using the least square method to obtain the photoelectric coefficient and the Compton coefficient.

18. The system of claim 10, wherein the detectors at the second tier are provided behind the detectors at the end parts and the central part of the first tier.

* * * * *